(12) United States Patent
Gilmore (10) Patent No.: US 7,832,119 B2
(45) Date of Patent: Nov. 16, 2010

(54) FIRST METATARSAL HEAD LIFT ORTHOTIC

(75) Inventor: Andre Gilmore, Lakewood, WA (US)

(73) Assignee: Solution Source, Lakewood, WA (US)

( * ) Notice: Subject to any disclaimer, the term of this patent is extended or adjusted under 35 U.S.C. 154(b) by 941 days.

(21) Appl. No.: 11/676,489

(22) Filed: Feb. 19, 2007

(65) Prior Publication Data
US 2007/0193071 A1 Aug. 23, 2007

Related U.S. Application Data

(60) Provisional application No. 60/774,767, filed on Feb. 17, 2006.

(51) Int. Cl.
*A43B 13/38* (2006.01)
(52) U.S. Cl. .............. 36/44; 36/143; 36/174; 36/180
(58) Field of Classification Search ......... 36/44, 36/142, 143, 144, 173, 174, 176, 178, 180, 36/181
See application file for complete search history.

(56) References Cited

U.S. PATENT DOCUMENTS

| | | | |
|---|---|---|---|
| 1,731,225 A | 10/1929 | Schneider | |
| 1,837,488 A | 12/1931 | Francis | |
| 1,847,973 A | 3/1932 | Morton | |
| 2,255,100 A * | 9/1941 | Brady | 36/173 |
| 2,616,190 A * | 11/1952 | Darby | 36/144 |
| 2,857,689 A * | 10/1958 | Van Ostrom et al. | 36/176 |
| 3,861,398 A | 1/1975 | Leydecker | |
| 4,747,989 A | 5/1988 | Peterson | |
| 4,813,159 A | 3/1989 | Weiss | |
| 4,940,046 A * | 7/1990 | Jacoby | 602/30 |
| 4,955,148 A | 9/1990 | Padilla | |
| 5,014,706 A | 5/1991 | Philipp | |
| 5,036,851 A | 8/1991 | Cohen | |
| 6,000,147 A * | 12/1999 | Kellerman | 36/44 |
| 6,026,599 A | 2/2000 | Blackwell | |
| 6,092,314 A * | 7/2000 | Rothbart | 36/144 |
| 6,170,176 B1 * | 1/2001 | Clough | 36/140 |
| 6,182,380 B1 * | 2/2001 | Liley | 36/71 |
| 6,205,685 B1 * | 3/2001 | Kellerman | 36/44 |
| 6,238,359 B1 | 5/2001 | Anderson | |
| 6,253,469 B1 | 7/2001 | Atlani | |
| 6,412,198 B1 | 7/2002 | Rothbart | |
| 6,453,578 B1 | 9/2002 | Yung | |
| 6,502,330 B1 | 1/2003 | David | |
| 6,513,264 B2 | 2/2003 | Sinaie | |
| 6,618,960 B2 | 9/2003 | Brown | |
| 6,874,258 B2 * | 4/2005 | Clough et al. | 36/144 |
| 6,938,363 B1 * | 9/2005 | Clough | 36/140 |
| 2004/0181976 A1 * | 9/2004 | Copeskey et al. | 36/145 |

* cited by examiner

*Primary Examiner*—Marie Patterson
(74) *Attorney, Agent, or Firm*—Dwayne E. Rogge; Hughes Law Firm, PLLC (57) ABSTRACT

A foot support device where the first metatarsal is raised with respect to the second through fifth metatarsals with a substantially horizontal support surface, the foot support device further having an arch support portion, the first metatarsal support allowing for a proper foot and ankle alignment for bipedal motion as well as standing.

29 Claims, 4 Drawing Sheets

FIG. 8F form a heel cup that is adapted to surround a posterior portion of a foot. In a different embodiment of the postural foundational alignment device, a first metatarsal base surface is positioned beneath the first metatarsal engagement surface at a distance which is greater than the distance between the second-fifth metatarsal engagement surface and a second-fifth metatarsal base surface.
FIRST METATARSAL HEAD LIFT ORTHOTIC

RELATED APPLICATIONS

This application claims priority of U.S. Provisional Ser. No. 60/774,767, filed Feb. 17, 2006.

BACKGROUND OF THE INVENTION

Orthotics and foot orthoses are available in a variety of forms addressing support or accommodate that which exists. The focus of those past designs was to support the arch only, always with forethought that the arch is the major issue of misalignment to the foot. Various forms of arch supports have been found in the prior art, along with other support devices in an attempt to bio mechanically align the foot and subtalar joint.

As described further here in, the disclosure recites a method for dynamically providing mechanical alignment of the foot/subtalar joint. All other prior art addressing only static alignment to the foot, i.e., the foot standing still.

As described herein, a Postural Foundational-Alignment System is provided to engage the first metatarsal head in a manner such that the greater toe along with the metatarsal head of the greater toe is lifted a certain height affecting the subtalar joint and other proximal joints above the base of the feet/foundation.

SUMMARY OF THE DISCLOSURE

An postural foundational alignment device attached to support the middle foot and anterior foot portions, the interior foot portion comprising a first metatarsal and first phalanges and second-fifth metatarsals and second-fifth phalanges. The postural foundational alignment device comprises a front region having a forefoot engagement surface comprising a first metatarsal engagement surface to support a first metatarsal and first phalange of the anterior foot portion, and further comprising a second-fifth metatarsal engagement surface adapted to engage the second-fifth metatarsals and second-fifth phalanges.

The surface of the first metatarsal engagement surface is positioned higher relative to the second-fifth metatarsal engagement surface and adapted to vertically raise the first metatarsal and first phalanges with respect to the second-fifth metatarsals and phalanges where the first metatarsal engagement surface is substantially level. The postural foundational alignment device further includes a metatarsal arch portion adapted to engage the middle foot region where the metatarsal arch portion is provided with an arch support that extends forwardly to the first metatarsal engagement surface.

In another form, the postural foundational alignment device is made where the arch support extends rearwardly to form a heel cup that is adapted to surround a posterior portion of a foot. In a different embodiment of the postural foundational alignment device, a first metatarsal base surface is positioned beneath the first metatarsal engagement surface at a distance which is greater than the distance between the second-fifth metatarsal engagement surface and a second-fifth metatarsal base surface.

In another form of the device mentioned above, the first metatarsal base surface and the second-fifth metatarsal base surface is not contiguous where an abrupt portion provides a more drastic change in elevation between these two surfaces. In alternative embodiment, the first metatarsal engagement surface and the second-fifth metatarsal engagement surface collectively comprise a forefoot engagement surface which is in a substantially continuous plane when pressure is not applied thereto.

In other forms of the postural foundational alignment device, the arch support may have a lower support surface that is contiguous with the first metatarsal base surface. Additionally, the first metatarsal base surface and the second-fifth metatarsal base surface may not be not contiguous surfaces.

In this form, the lower support surface of the arch support may extend in the posterior portion to form a heel cup, and the heel cup may have a lateral region that extends in the anterior direction just short of the cuboid and the base region of the fifth metatarsal. The posterior portion of the foot is adapted to rest within the heel cup of the postural foundational alignment device.

In various other forms, a heel engagement surface is positioned above the heel cup and is substantially contiguous when pressure is not applied thereto, or the heel engagement surface may be rested between a medial and lateral raised area to support the posterior portion of the foot. The postural foundational alignment device may be made from a material having a durometer rating between 30 and 50.

DETAILED DESCRIPTION OF THE PREFERRED EMBODIMENTS

As described herein, there is shown an embodiment where the first metatarsal head is raised with respect to the surrounding areas. In a preferred form, a surface is substantially orthogonal to the flux field of gravity (of course with localized surface variations as an option or angled about a lateral axis).

It is believed by the applicant that as the foot steps off, the greater toe especially, that toe pronates or rolls more to the inside in a twisting torquing shearing moment past 4 degrees of this a normal acceptable inside roll. The human body in its innate wisdom also recognizes in some people that instead of allowing the toe to potentially pronate excessively it will protect or guard against this roll to the inside and brace or restrict itself and hold the foot at the toe off phase of motion thus to hold the foot in a "supinated" position. Having a higher arch or walking too long along the outside or lateral border of the foot.

As a result of this excessive (in one form, more than four degrees of internal roll) pronation motion, a "shortening" of the inside portion of the foot occurs. In the typical gait phase of walking the human body strikes at the heel contact phase of forward motion affecting a loss of alignment as the center of gravity or the weight bearing line passes over the Sustentaculum tali area of the calcaneus, then on to the navicular bone, the first cuneiform bone, the greater metatarsal head including the sesamoid bones of the great toe and along the MIP, PIP, DIP and out to the very distal edge of the great toe an, excessive pronation motion can occur along this area that describes the "medial column" border of the medial (inside) of the foot.

It is believed that such an unbalanced, unstable non symmetrical biomechanical human foundation can contribute to further negative affects of health through out the human body.
Areas of negative affectations can result in the following:
Musculoskeletal imbalances
Over worker muscles,
Under worker muscles
Contracted tight muscles
Stretched (past their normal effective length) muscles
Painful point of origin and insertion attachments
Forward leaning posture
Rounded shoulders
Sway backs,
Kyphotic upper backs
Incongruent joint alignment
Excessive torque and joint wearing points of abnormal contact
Spinal dysfunctions such as scoliosis, pinched nerves, slipped discs, spondylolesis, boney spurs,
Lower, middle, upper back, shoulder, neck, head strains as sprains felt as "pain"
Bio-implosion of the thoracic cavity collapsing on itself affecting abnormal compressive forces on the lungs, heart, and other organs of the thoracic cavity.

It is believed that such negative issues can occur when the foundation of the foot is not in dynamic symmetrical alignment, i.e., right foot to left foot is not symmetrically aligned to each other in the full dynamics of forward motion.

Figure 5:
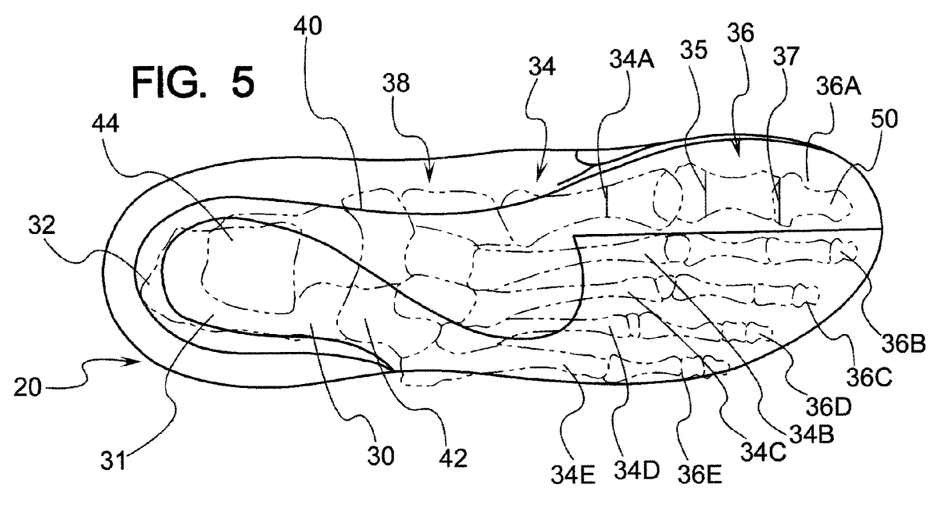
FIG. 5 shows a bottom view of the orthotic with the bone structure superimposed thereabove as a hatched line.

Present analysis indicates that raising the first metatarsal head and throughout the greater toe with its special contouring can be at the PIP joint area designated as seen in FIG. 5 at 35, and the DIP joint area together or just the DIP area taper at the junction 37 in FIG. 5. and orthogonal to the flux field of gravity design has the synergistic benefit of stimulating a straighter posture alignment of the human frame, providing a sulcus raise, a metatarsal-transverse arch-raise, relief of painful excesses boney met head pressure from the other (2-5) metatarsal heads in forward motion, correcting excessive internal or external rotation of the foot on the ground, leveling the pelvic girdle where one side may have been longer or shorter asymmetrically. This change in placement of the significant lift of the first metatarsal head lift orthotic (FMHLO) provides a greater distribution of lifting forces under the remaining parts of the boney structures of the foot particularly in the navicular, all cuneiforms, cuboids, metatarsal shafts, and corresponding joint links. Further, the great toe is placed in a more symmetrical balanced alignment during the various phases of motion when the first metatarsal head is raised with respect to the adjacent metatarsals.

Dynamic Symmetrical Alignment Balance (DSAB) can only be applied to this type (e.g. FMHLO) of design consideration, in particular the great toe raise especially from the metatarsal head under the sesamoid bones of the great toe and following along to the distal tip of the toe with its fundamental orthogonal shape and distal tapering from the PIP (proximal Interphangeal phalanges) demarcation 35 in FIG. 5 and the DIP joint area 37, or solely the DIP joint area 37, in a proportion to the percentage of height in the raised patentable platform.

The resulting mechanical changes that gradually occur over a short time frame beneficial to the human body are correcting forces that stimulate positive changes to the negative effect listed above. It can further be observed that a more "natural" format of forward motion will occur such that the feet/foundation will walk with a closer base of gait, not one foot will be more or less externally or internally rotated out or in than the other, respectively, knock knee formations will be decreased, bowlegged curves will be lessened.

There will now be a general discussion of the human body and particularly the lower boney structural portion (the feet/foundation). It should be noted that a standing (static) erect body has a different shape of the boney foot structures than does a moving (dynamic) boney foot structure. Therefore, the postural foundational alignment insole device must provide functional stimulation correction/support taking into consideration the static verses the dynamic shapes of the boney feet/foundation for a most desirable feet/foundation stabilizing effect. The feet wearing this particular design concept of the FMHLO will strengthen over a short period of time in the musculature in and around the foot and throughout the other postural muscles.

Referring ahead to FIG. 5, there is shown an outline of a skeletal human foot 30. In general, the bones in a human foot are comprised of a calcaneus 32, the metatarsals 34 and the phalanges 36. Aft of the metatarsals 34 are the cuneiform bones 38 which are adjacent to the navicular 40 and the cuboid 42. Positioned after the navicular and the cuboid 40 and 42 is the talus indicated at 44. It should be noted that the tibia (not shown) is positioned on top of the talus 44.

As further shown in FIG. 5, there is a line indicated at 35 which generally indicates the location of the PIP joint, and the approximate location indicated at 37 is the DIP joint.

With the general background of the bones in place, it should be noted that the majority of the population are not "unwound" from the talus 44 in relationship to the calcaneus 32 where a baby's feet do not fully unwind and are not properly pronated to get the first metatarsal head "on the ground". Therefore, even when the ankle is somewhat neutral, there is not sufficient lift in the metatarsal head to properly put the ankle in a neutral joint alignment.

Figure 1:
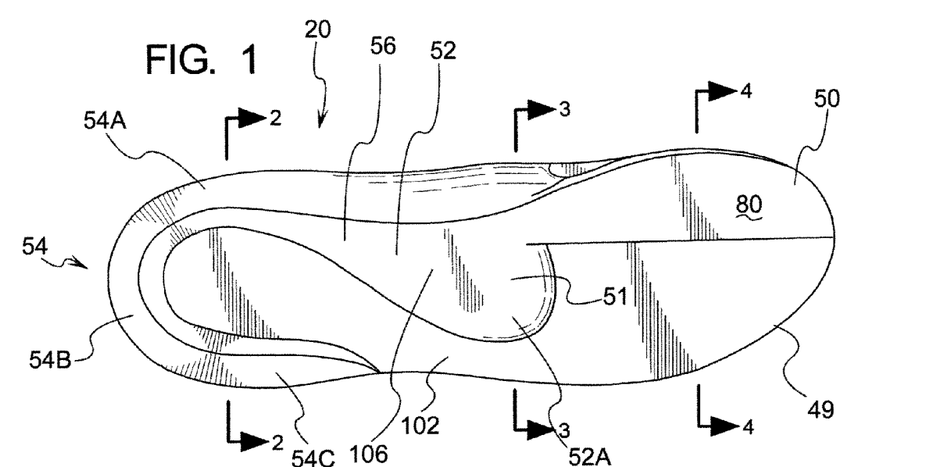
FIG. 1 shows a bottom view of an postural foundational alignment device.

As shown in FIG. 1, there is a bottom view of the orthotic device 20. As shown in this figure, the orthotic 20 device comprises a forefoot lift region 50 which is described in greater detail below. The general area indicated at 51 indicates the metatarsal arch portion. The region indicated at 52A extends laterally outwardly and flares downwardly to the outer metatarsal portions. The heel cup generally indicated at 54 which is optional in one form, is divided into sections 54A, 54B and 54C which show the medial, posterior and lateral regions surrounding the calcaneus portion on its medial, posterior and lateral borders 31 (see FIG. 5) of the foot. The posterior portion of the heel and the medial portions are supported at 54B and 54A. Further, the lateral repositioning of the user's heel can be controlled at 54C. The medial portion of 54A and the forward portion of the section 54A extends to the medial arch to the sustentaculum tali. In general the heel cup encompasses the posterior aspect of the calcaneus around the medial and lateral aspects of the calcaneus to just proximal or behind the weight bearing line of the sustentaculum tali on the medial side of the foot and cupping around the cuboid on the lateral side of the foot just proximal to the body of the fifth metatarsal head. The heel cup does not lift the heel-calcaneus bone but rather cradles it. In one form it acts as a guide to the heel at heel contact to mid-stance simulating a more vertical heel support mechanism.

Now referring to the outer lateral portion 54C, the heel cup extends around the cuboid 42 (see FIG. 5) to the lateral portion of the foot and is just proximal to the body of the fifth metatarsal head. Therefore, the end portion in the preferred form is just laterally outside of the cuboid and proximal to the fifth metatarsal head as shown in FIG. 5. In one form the portions 54A, 54B and 54C encapsulate the entire calcaneus. In a preferred form, the sustentaculum tali of the foot (not shown) is in proper engagement where the calcaneus is supported at this merger area between the heel cup portion 54A and the metatarsal arch portion 52 generally at the region indicated at 56.

With the foregoing description in place, there will now be a more detailed discussion of the forefoot lift region 50.

The metatarsal region 34 is comprised of the first through fifth metatarsal bones indicated at 34A-34E as shown in FIG. 5. The corresponding phalanges connected to each metatarsal head are numbered in a corresponding manner, 36A-36E. It should be noted that FIG. 5 shows a bottom view where the bones of the foot are shown in a hatched line where this would be a left foot and a left insole. However, in one form, the edge surfaces 88 (see FIG. 4) of the forefoot lift area can be positioned in the upper portion, where as shown in FIG. 5, the very surfaces defining the surface to engage the foot are positioned in a manner where FIG. 5 would be the right insole with the right foot positioned thereon.

Figure 4:
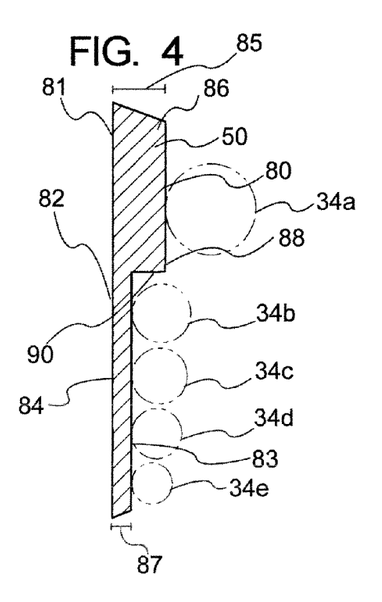
FIG. 4 shows a cross-sectional view at the forefoot lift region showing the area which lifts the first metatarsal head of the foot taken at line 4-4 of FIG. 1.

As shown in FIG. 5, it can be seen how the forefoot lift region 50 is positioned beneath the first metatarsal head area indicated from 34A to 35 and the first phalange (the big toe bone) is indicated at 36A. As shown in FIG. 4, the cross-sectional view shows the forefoot lift region 50. In general, the front base region 49 of the postural foundational alignment device 20 as mentioned before comprises the forefoot lift region 50. The first metatarsal base surface indicated at 80 is substantially orthogonal to the flux field of gravity. Another way of describing the surface 80 is that it is substantially level. The forefoot foot engagement surface 82 (as shown in FIG. 4) comprises a first metatarsal engagement surface 81 and a second through fifth metatarsal engagement surface 84. It should be noted that the surfaces 81 and 84 extend distally to the corresponding phalange regions as indicated in FIG. 5.

Referring back to FIG. 4, the first metatarsal base surface 80 has a medial portion 86 and a laterally outward portion 88. In one form, the laterally outward portion has an abrupt edge 90 creating a fairly significant change in elevation from the first metatarsal base surface 80 to the second-fifth metatarsal base surface 83. The abrupt edge 90 need not be a perpendicular surface as shown in FIG. 4 to the surfaces 80 and 83. Rather, it could be a transition of some sort with an angled surface where a majority of the weight-bearing surface 80 is more or less level and distinctly on a different elevation than the surface 83.

Figure 4A:
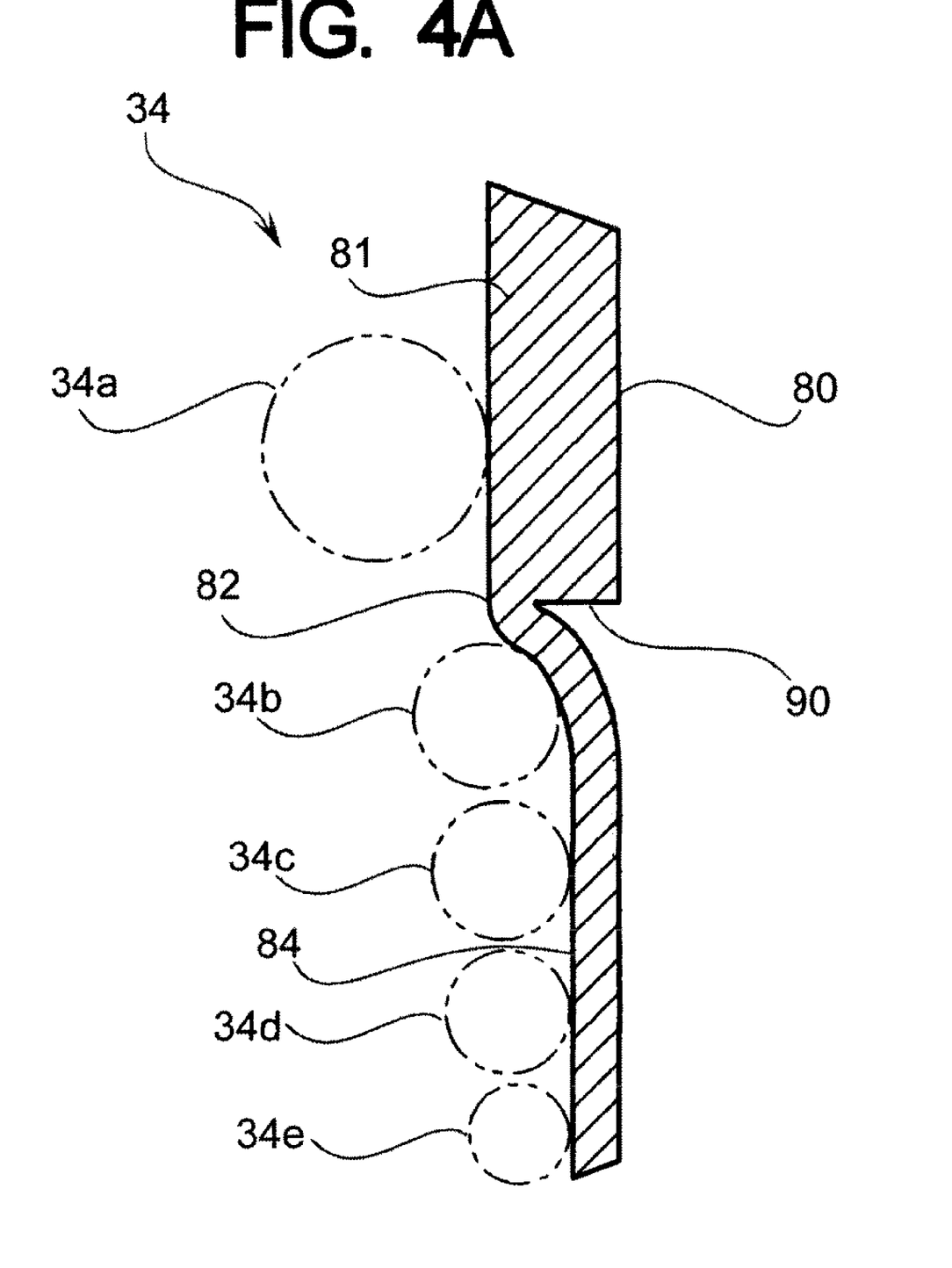
FIG. 4A shows a cross-sectional view at the forefoot lift region showing the area which lifts the first metatarsal head of the foot taken at line 4-4 of FIG. 1 where the metatarsals are positioned in a preferred form.

As shown in FIG. 4, the metatarsals 34 are schematically indicated at 34a-34e. FIG. 4 shows one embodiment where the foot is positioned on the side of the orthotic 20 with the abrupt edge 90 positioned upwardly. Now referring to FIG. 4A, the metatarsals schematically shown at 34a-34e are positioned upon the forefoot engagement surface 82 where it can be appreciated that the second through fifth metatarsals' engagement surface 84 is deflected downwardly and the first metatarsal 34a is raised with respect to the second through fifth metatarsals 34b-34e. The insole 20 can be comprised of a material that contributes to flexibility. In some forms the metatarsal lift area can have a lower durometer rating (e.g. 15-25) and arch region can durometer of up to, say for example, 60 durometer rating. The durometer rating can be changed by mixing a "C-Mix" to adjust the durometer rating. Of course other materials and methods can be used to comprise the orthotic 20.

Figure 2:
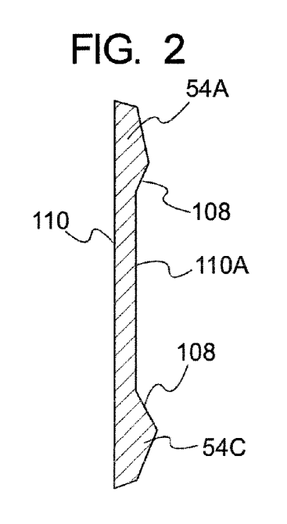
FIG. 2 shows a cross-sectional view of the postural foundational alignment device and a heel cup region taken at line 2-2 of FIG. 1.
Figure 3:
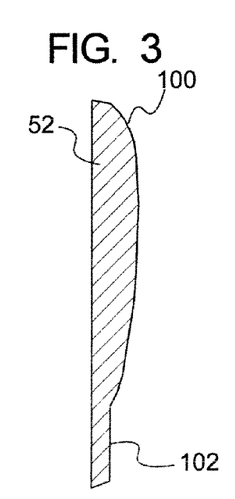
FIG. 3 shows a cross-sectional view of the postural foundational alignment device at a metatarsal arch portion taken at line 3-3 of FIG. 1.

Referring now to FIG. 3, there is shown a metatarsal arch 51 portion in cross-section. In general, this portion has a medial region 100 and a lateral portion 102. In general, the medial region is sufficiently higher raised above the lateral portion 102 to provide a transverse metatarsal arch support. As shown in FIG. 1, the arch support lower support surface 106 in one form is contiguous with the first metatarsal base surface 80. Further, the lower support surface 106 in one form continues the role posteriorly to the inner region of the heel cup 54 as seen in FIG. 2.

Figure 7:
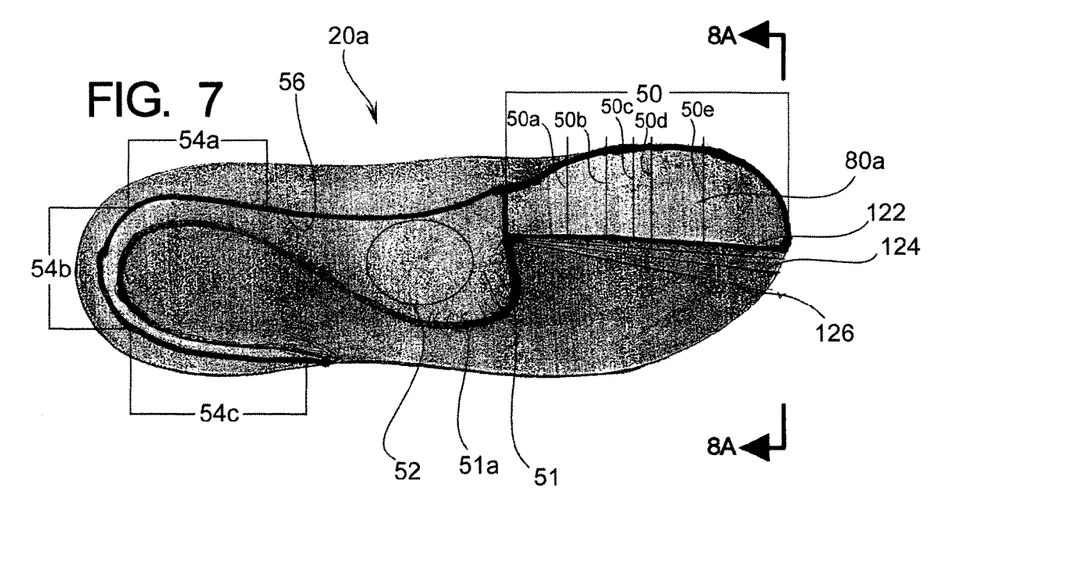
FIG. 7 shows a view of another embodiment where the orthotic can be adjusted with the shim inserts.

There will now be a more detailed description of the forefoot lift region with reference to FIG. 7. In general, FIG. 7 shows another embodiment utilizing an adjustable system described further herein; however, the forefoot lift region 50 will be further described as to the various attributes thereof. The regions 50a, 50b and 50c indicate the general area which engages the lift for the first metatarsal, which can vary between 0.25 mm to 20 mm in the broad range. In general, a forward taper can occur to the PHP joint at 50d and extend to the forward region of the support 20, or the DIP joint 50. The metatarsal head is generally raised at the portion 50b, and the proximal portion of this metatarsal head area is indicated at 50c. It should be noted that these areas are similar to the regions 34a and 35 as shown in FIG. 5.

With regard to the forward taper of the first metatarsal lift region 50, as noted above, the taper can begin at the PHP joint indicated at 50d or at the beginning of the DIP joint at 50. Present analysis indicates that combining the taper starting at the PHP area at 50d and transcending it downwardly to the DIP area at 50e has beneficial effects on the proprioceptive feedback for the patient. Alternatively, the taper can begin at the DIP location at 50e to the distal end of the great toe.

Figure 6:
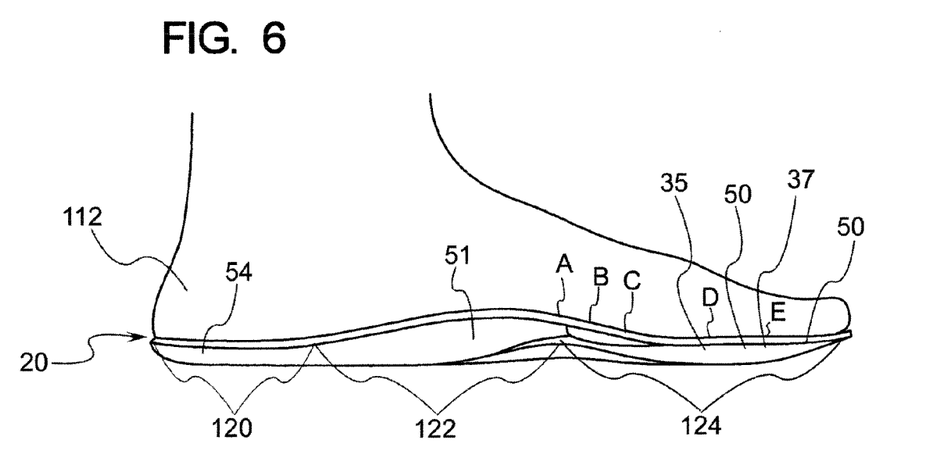
FIG. 6 shows a side view of the foot positioned on the postural foundational alignment device.

Now referring to FIG. 2, the heel cup 54 is shown in cross-section where the medial and lateral regions 54A and 54C are shown. A heel cup engagement surface 110 in one form is a substantially contiguous surface which is adapted to be deformed when pressure is placed thereon such as from the heel of the foot. As shown in FIG. 6, a heel 112 can depress the orthotic downwardly to properly position the calcaneus within the heel cup region 54. Referring back to FIG. 2, alternatively the heel engagement surface could be indicated at 110 where in this form the foot engaging surfaces are not contiguous but rather each orthotic is essentially turned upside down and switched from one foot to the other. With this embodiment, the surface indicated at 80 in FIG. 4 would function as the first metatarsal engagement surface where the foot is placed directly thereon.

Referring back to FIG. 6, it can be seen how the posterior portion 120 of the foot is supported by the optional heel cup 54. The middle portion 122 is supported by the arch support portion 52 and the anterior foot portion is supported by the forefoot lift region in its entirety 50 to raise the first metatarsal head and big toe with respect to the adjacent metatarsals. With the foregoing description in mind, there will be further discussion of the dynamic effects (as well as the static standing effects) of the orthotic 20 as it interfaces with the foot of the individual.

In one form the orthotic 20 supports the foot such that it stimulates the foot/foundation to change its position and/or placement on the ground under the human frame (aligning the foot to knee, etc.) sending a message or proprioceptive feedback loop through the nerve (nervous) system to the brain to affect positive postural changes. The cause-and-effect neural response synergistically operates upon the body for the orthotic support device 20 to create foot alignment. The medial column extension of the foot can provide a extra support to the medial column bones such as the cuneiform, navicular, and sustentaculum tali when the foot is aligned. In such alignment, the sustentaculum tali operates as a lever from the calcaneus and is adapted to engage the talus for proper foot support and alignment.

Feet while standing and feet in motion take much stress. Muscles, tendons, ligaments, simply the muscoskeletal system as a whole is under a great amount of negative alignment stress when the feet/foundation are not symmetrically balanced to the ground. Generally, when the body is in motion, initial weight bearing contact is made at heel contact the weight bearing line and center of gravity of the body passes the heel forward or moves distally through the calcaneus to the mid-foot to the forefoot where one-third (⅓) of the forward weight bearing load is carried through the metatarsal head of the great toe, and the other two-thirds (⅔) is distributed throughout the remaining 2-5 metatarsals, phalanges, and met heads, and then to the final gait phase of toe-off through the distal end of the great toe. The crucial alignment of the great toe at toe-off affects the foundational support to the rest of the body. Pronation is seen at this final phase of the final gait cycle.

In one form of a preferred embodiment as discussed in detail above, the heel cup stabilizes motion of the posterior portion of the calcaneus (hell) bone area 120 of the foot as shown in FIG. 6. The mid foot is in control by the arch support region 122 and the forefoot lift region 124 and the entire forefoot lift area 50 provides a "toe off" dynamic symmetrical alignment that is designed to contribute to a straighter balanced aligned posture for the individual wearing the orthotic 20. This allows for a straighter, more dynamic postural alignment of an individual wearing the orthotic 20. As the foot rolls to the mid-foot section, the arch guides the foot to the forefoot lift which runs from the distal toe to about 3 millimeters behind the metatarsal head or sesamoid bones, approximately 3 millimeters proximal (longitudinally rearwardly to the metatarsal head). The foot rolls up to the major forefoot lift at the metatarsal head and the sesamoid bones. The forefoot lift 50 is substantially level and is not wedged to provide a stable upper platform for supporting the first metatarsal head. However, in the longitudinal direction, in one form the forefoot lift will taper from the PIP joint to the DIP joint or from the DIP joint to the distal end of the toe. The amount of taper to the toe region can be none at all (i.e. 0%) where it is level with the surrounding surface or a decline in thickness of, for example, a 50% drop from the metatarsal highest portion to the end toe region.

Now referring to FIG. 6, indicated at portion E is the beginning of the DIP joint taper and at the portion D can be the beginning of the PIP joint taper and can taper into the DIP joint along the longitudinal direction to the distal end of the toe. As described above, it is desirable to have this taper for various plantar flexion during dynamic movement and walking. This taper flattens in a longitudinal direction and does not substantially alter in a lateral direction. The section between D to B as shown in this figure is the metatarsal lift at the first metatarsal head which is substantially flat and level with respect to the ground. This portion is underneath the sesamoid bones area and extends back behind the metatarsal sesamoid bones as indicated at point B as shown in FIG. 6.

Therefore the reference points A-E defines the forefoot lift 50. The portion C is the apex of the metatarsal head which is an important part of the foot and is the beginning part of the distal portion of the arch of the individual's foot. The height 85 (see FIG. 4) of the forefoot lift 50 can be between 0.25 mm up to 20 mm in the broader range of the height with respect to the surrounding portion of the orthotic (near phalanges 2 through 5). A more desirable range is 0.5 mm to 5 mm.

The first metatarsal engagement surface 81 as shown in FIG. 4 is defined as a region that raises the first metatarsal head with respect to the adjacent metatarsal heads at a substantially level surface. The first metatarsal engagement surface 81 raises the first metatarsal head without substantially interfering with the other metatarsals and phalanges. In one form, it is parallel with the base of a shoe or other foot support, however, certain angular deviations are within the broader scope by way of manufacturing intolerance or a desirable slight longitudinally extending angle. However, the overall operation of the lift should be so that it provides a substantially parallel vertical lift in the lateral direction of the metatarsal head and the two sesamoid bones (not shown) in the first metatarsal.

A substantially level surface 83 in the lateral direction as shown in FIG. 4 creates less tissue damage to the foot by way of frictional engagement. When the height indicated at 85 in FIG. 4 is properly set, present analysis and experimentation indicate less callusing than in other prior art devices. In essence, there is less shearing of the tissue when the height 85 of the vertical lift is at a proper elevation with respect to the height 87 provided for the second through fifth metatarsals. It should be noted that the lateral inward width of the raised metatarsal region should essentially only be under the first metatarsal head and not in the second metatarsal head. Empirical analysis and feedback from patients indicate that they can detect when the lift is positioned excessively laterally outwardly and there is any pressure on the second metatarsal head. However, there could be a taper that transitions laterally outward near the abrupt edge region 90 as shown in FIG. 4 but does not engage or supply any significant amount of force to the second metatarsal head.

Therefore in the front region 49, the transition from the elevated portion of the forefoot lift region 50 having a height indicated at 85 can extend laterally outwardly toward the second and possibly the third metatarsal heads for purposes of transitioning to the height indicated at 87 in extreme cases; however, the first metatarsal head is the metatarsal head to be in positive engagement or forceful lifting engagement by way of the height differential between distances 85 and 87.

With the forgoing technical description in mind, present observation and analysis has indicated that placing and raising the metatarsal head with a substantially level surface has a positive alignment effect throughout the body. The individuals having a first metatarsal lift on the forefoot lift region 50 acting on the foot tend to have their posture straightened. Further, when a slight arch support in the midfoot section is provided, there is a further synergistic effect where the individual's body relaxes and stimulates the midfoot and hind foot stand in a more vertical alignment. Further, a heel cup provides a proprioceptive feedback to the brain to stand more vertically.

As shown in FIG. 7, there is shown another embodiment where the orthotic 20a is shown in another form where certain modifications can take place by the end user. The first metatarsal base surface 80a can extend in the lateral outward direction by way of repositioning the surface to, for example, the lateral outward lines 122, 124 and 126. Further, the height of the first metatarsal lift indicated at 85i can be adjusted as further described herein.

Figure 8A:
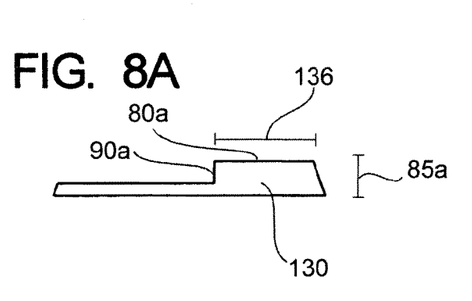
FIGS. 8A-8F show various views taken along line 8A-8A of FIG. 7 where it can be seen that various lateral and vertical shims are positioned to adjust the nature of the first metatarsal head lift orthotic.

As shown in FIG. 8A, there is a base support unit 130 which provides an initial first metatarsal base surface 80a. The surface further has an abrupt edge 90a to allow for a lift of the first metatarsal as described above and shown in, for example, FIG. 4A. If the user or a medical professional decides that the first metatarsal requires additional lift with respect to the adjacent second through fifth metatarsals, a first metatarsal shim can be positioned as indicated at 132 in FIG. 8C. By adding a shim, the height of the first metatarsal indicated at 85i' increases with respect to the initial height indicated at 85a, as shown in FIG. 8A.

Referring now back to FIG. 8A, the metatarsal support base width 136 can be adjusted. For example, as shown in FIG. 8B, this width is increased as indicated at 136' by adding a width shim 138.

Figure 8B:
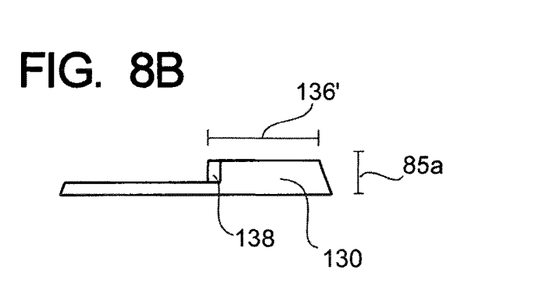
Figure 8C:
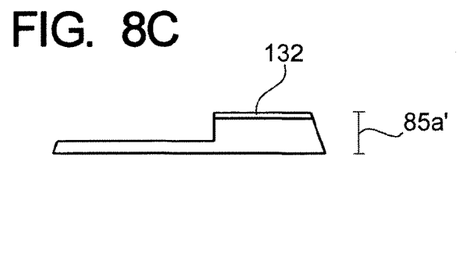
Figure 8D:
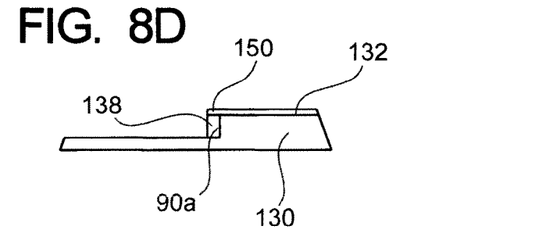

Still referring to FIG. 8B, it can be seen how the base support unit 130 is provided. In this form, a width shim 138 is positioned adjacent to the abrupt edge 90a. Further, the first metatarsal shim 132 is positioned thereabove.

Figure 8E:
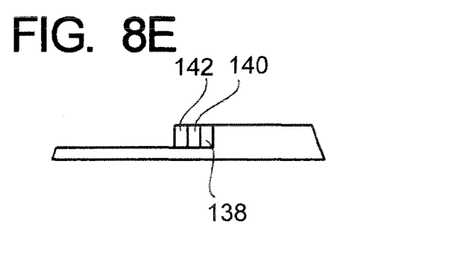
Figure 8F:
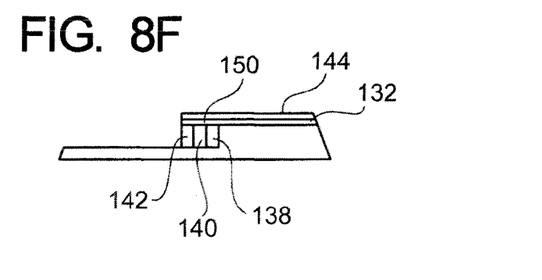

Now referring to FIGS. 8E-8F, there is shown another form where additional shims 140 and 142 are positioned in the lateral direction. As shown in FIG. 8F, additional first metatarsal lift shims, such as that shown at 144, can be added to provide a customized orthotic to provide a postural foundation for the user. Of course, the shims can be attached by a variety of methods, such as by way of an adhesive or the like. Further, with a configuration similar to that shown in FIG. 8B and FIG. 8F, the lateral width shims 138, 140 and 142 are bound therein by way of the surface 150 being in engagement with the surface of the shim 132.

In one form of implementing the orthotic, a practitioner would watch the ankles and knees to observe any difficulty in twisting, collapsing or other nonalignment issues. Another form of inspecting the patient is to have them stand up and invite them to walk back and forth to observe any pattern of walking or collapsing of the joints. Further inspection can be engaged on the ileum and the posterior iliac spine to ensure that these regions are level. Other examination practices can include measuring the foot arch and length and having the patient bend at the knees by shifting their weight forward and observing the action of their ankles, heels and knees.

At this point, the practitioner can raise the big toe and the first metatarsal and observe the alignment to ensure the patient's knees are not collapsing or pulling apart. For example, the practitioner can utilize various modular lift mechanisms, as shown in the figures noted above, to configure a proper orthotic. Of course, in cases where one leg is longer than the other, the entire orthotic (one of the orthotics) can be raised to bring the hips into proper alignment. In general, it is advised that the practitioner communicates with their patient and observes the patient's body during this iterative process.

The practitioner can then take the data based upon this improvised orthotic utilizing the various shims and preset arches, and communicate this to a central manufacturing facility which can return the orthotic to the practitioner or directly to the patient. The practitioner could be part of a franchise arrangement or otherwise under contract when utilizing the postural foundation alignment device.

In another form, a stock model of a postural foundation alignment device can be provided, and various shims with adhesive portions are sold therewith so the individual can make their own adjustments. In this form, the individual could be instructed by way of written instructions and perhaps through audiovisual presentation, such as a DVD, to walk towards a mirror where self observation can be conducted by, say, performing the motion of the knees in the lateral direction. In this form, the individual can adjust the shims in the lateral direction if, for example, they have a narrower foot, and further can adjust the first metatarsal engagement surface and the height thereof with respect to the second through fifth metatarsals.

While the present invention is illustrated by description of several embodiments and while the illustrative embodiments are described in detail, it is not the intention of the applicants to restrict or in any way limit the scope of the appended claims to such detail. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicants' general concept.

The invention claimed is:

1. An postural foundational alignment device attached to support the middle foot and anterior foot portions, the interior foot portion comprising a first metatarsal and first phalanges and second-fifth metatarsals and second-fifth phalanges, the postural foundational alignment device comprising:
   a) a front region having a forefoot engagement surface comprising a first metatarsal engagement surface to support a first metatarsal and first phalange of the anterior foot portion, and further comprising a second-fifth metatarsal engagement surface adapted to engage the second-fifth metatarsals and second-fifth phalanges,
   b) where the surface of the first metatarsal engagement surface is positioned higher relative to the second-fifth metatarsal engagement surface and adapted to vertically raise the first metatarsal and first phalanges with respect to the second-fifth metatarsals and phalanges where the first metatarsal engagement surface is substantially level,
   c) a metatarsal arch portion adapted to engage the middle foot region where the metatarsal arch portion is provided with an arch support that extends forwardly to the first metatarsal engagement surface and laterally outward beyond the first metatarsal engagement surface.

2. The postural foundational alignment device as recited in claim 1 where the first metatarsal engagement surface is operatively configured to be positioned beneath the first metatarsal to engage a DIP joint where the first metatarsal base surface tapers downwardly to the distal portion of the first phalange.

3. The postural foundational alignment device as recited in claim 2 where the taper of the first metatarsal engagement surface extends from a full height to less than 25% of the full height near the distal end of the first Proximal Interphangeal Phalanges.

4. The postural foundational alignment device as recited in claim 2 where the taper of the first metatarsal engagement surface extends from the DIP joint of the first phalange to a PIP joint of the first phalange.

5. The postural foundational alignment device as recited in claim 1 where the arch support extends rearwardly to form a heel cup that is adapted to surround a posterior portion of a foot.

6. The postural foundational alignment device as recited in claim 1 where a first metatarsal base surface is positioned beneath the first metatarsal engagement surface at a distance which is greater than the distance between the second-fifth metatarsal engagement surface and a second-fifth metatarsal base surface.

7. The postural foundational alignment device as recited in claim 6 where the first metatarsal base surface and the second-fifth metatarsal base surface is not contiguous where an abrupt portion provides a more drastic change in elevation between these two surfaces.

8. The postural foundational alignment device as recited in claim 7 where the first metatarsal engagement surface and the second-fifth metatarsal engagement surface collectively comprise a forefoot engagement surface which is in a substantially continuous plane when pressure is not applied thereto.

9. The postural foundational alignment device as recited in claim 1 where the arch support has a lower support surface that is contiguous with the first metatarsal base surface.

10. The postural foundational alignment device as recited in claim 9 where the first metatarsal base surface and the second-fifth metatarsal base surface are not contiguous surfaces.

11. The postural foundational alignment device as recited in claim 10 where the lower support surface of the arch support extends in the posterior portion to form a heel cup.

12. The postural foundational alignment device as recited in claim 11 where the heel cup has a lateral region that extends in the anterior direction just short of cuboid and the base surface of the fifth metatarsal.

13. The postural foundational alignment device as recited in claim 12 where the posterior portion of the foot is adapted to rest within the heel cup of the postural foundational alignment device.

14. The postural foundational alignment device as recited in claim 13 where a heel engagement surface is positioned above the heel cup and is substantially contiguous when pressure is not applied thereto.

15. The postural foundational alignment device as recited in claims 12 where a heel engagement surface is rested between a medial and lateral raised area to support the posterior portion of the foot.

16. The postural foundational alignment device as recited in claim 1 where the postural foundational alignment device is made from a material having a durometer rating between 30 and 50.

17. A foot support device adapted to be positioned in footwear to support a foot, the foot support device comprising:
   a) a forefoot lift region where a forefoot engagement surface comprises a first metatarsal engagement surface and a second-fifth metatarsal engagement surface where when pressure is applied to the forefoot engagement surface the first metatarsal engagement surface is positioned higher than the second-fifth metatarsal engagement surface, the foot support device further comprising a metatarsal arch portion that is raised higher in the medial portion with respect to the adjacent lateral portion, whereas the first metatarsal engagement surface is substantially level, and
   b) a metatarsal arch portion adapted to engage the middle foot region where the metatarsal arch portion is provided with an arch support that extends forwardly to the first metatarsal engagement surface and laterally outward beyond the first metatarsal engagement surface.

18. The foot support device as recited in claim 17 where the metatarsal arch portion has a lower support surface that is contiguous a the first metatarsal base surface positioned vertically opposing the first metatarsal engagement surface.

19. The foot support device as recited in claim 17 where the first metatarsal base surface and the second-fifth metatarsal base surface are not contiguous surfaces.

20. A method of rotating an individual's foot out of the sagittal plane comprising the steps of:
   a) providing a postural foundational alignment device comprising a forefoot engagement surface having a first metatarsal engagement surface and a second through fifth metatarsal engagement surface,
   b) positioning the metatarsals of the individual upon the forefoot engagement surface where the first metatarsal is positioned on the first metatarsal engagement surface and the second through fifth metatarsals are positioned on the second through fifth metatarsal engagement surface where the first metatarsal engagement surface is substantially level and raised with respect to the second through fifth metatarsal engagement surfaces when the forefoot of the individual is placed thereon,
   c) providing a tarsal arch portion and engaging the middle foot region of the individual where the metatarsal arch is configured to raise the laterally inner tarsal of the individual with respect to the laterally outer tarsal, and
   d) the tarsal arch portion is adapted to engage the middle foot region where the tarsal arch portion is provided with an arch support that extends forwardly to the first metatarsal engagement surface and laterally outward beyond the first metatarsal engagement surface.

21. The method as recited in claim 20 where a height of the first metatarsal engagement surface is adjusted by adding a first metatarsal shim, thereby raising the first metatarsal further with respect to the second through fifth metatarsals.

22. The method as recited in claim 21 where a lateral shim is positioned adjacent to a forefoot lift region which comprises the first metatarsal engagement surface.

23. The method as recited in claim 22 where the lateral shim is positioned first adjacent to the forefoot lift region, and the first metatarsal shim is positioned on a first metatarsal base surface which is a part of the forefoot lift region and the first shim further engages the width shim.

24. The method as recited in claim 20 where the postural foundation alignment device is comprised of polyurethane having a hardness rating between 5-60 durometers.

25. The method as recited in claim 20 where the individual's foot is repositioned, remedying collapsing bones resulting in hyper-pronation of the foot with respect to the surrounding ground where the calcaneus at the sustentaculum tali, the navicular, the cuneiforms, and the midfoot arch are aligned to provide a proper rotation thereof partially vertically about a longitudinal axis of the individual's foot.

26. The method as recited in claim 20 where the individual's foot has at least a 4-degree amount of roll from the individual's great toe to prevent supination of the foot.

27. The method as recited in claim 26 where the degree of rotation of the foot from the sagittal plane is between 5-7 degrees with respect to the great toe.

28. The method as recited in claim 20 where a practitioner provides the postural foundation alignment device and adjusts the first metatarsal engagement surface by adding shims thereunder and observing the foot alignment.

29. The method as recited in claim 28 where data from the practitioner is sent to a central location for production of a permanent postural foundational alignment device.

* * * * *